US011607448B2

United States Patent
Qi et al.

(10) Patent No.: US 11,607,448 B2
(45) Date of Patent: Mar. 21, 2023

(54) WHOLE AVIAN-ORIGIN REVERSE GENETIC SYSTEM AND ITS USE IN PRODUCING H7N9 SUBTYPE AVIAN INFLUENZA VACCINE

(71) Applicant: SOUTH CHINA AGRICULTURAL UNIVERSITY, Guangdong (CN)

(72) Inventors: Wenbao Qi, Guangdong (CN); Ming Liao, Guangdong (CN); Yiqun Chen, Guangdong (CN); Huanan Li, Guangdong (CN); Bo Li, Guangdong (CN); Jiahao Zhang, Guangdong (CN); Ziwen Qiu, Guangdong (CN)

(73) Assignee: SOUTH CHINA AGRICULTURAL UNIVERSITY, Guangdong (CN)

( * ) Notice: Subject to any disclaimer, the term of this patent is extended or adjusted under 35 U.S.C. 154(b) by 0 days.

(21) Appl. No.: 17/726,577

(22) Filed: Apr. 22, 2022

(65) Prior Publication Data
US 2022/0370594 A1    Nov. 24, 2022

(30) Foreign Application Priority Data

May 24, 2021    (CN) .......................... 202110564096.4

(51) Int. Cl.
*A61K 39/145*    (2006.01)
*C12N 7/00*    (2006.01)
*A61K 39/00*    (2006.01)

(52) U.S. Cl.
CPC .............. *A61K 39/145* (2013.01); *C12N 7/00* (2013.01); *A61K 2039/5256* (2013.01); *A61K 2039/552* (2013.01); *C12N 2760/16121* (2013.01); *C12N 2760/16122* (2013.01); *C12N 2760/16134* (2013.01); *C12N 2760/16151* (2013.01); *C12N 2760/16171* (2013.01)

(58) Field of Classification Search
None
See application file for complete search history.

(56) References Cited

U.S. PATENT DOCUMENTS

2022/0370594 A1*  11/2022  Qi .......................... A61K 39/145

FOREIGN PATENT DOCUMENTS

| CN | 107753943 A | 3/2018 |
| CN | 110172452 A | 8/2019 |
| CN | 110218706 A | 9/2019 |
| EP | 3403671 A1 | 11/2018 |

OTHER PUBLICATIONS

CNIPA First Office Action corresponding to Application No. 202110564096.4; dated Jul. 6, 2021.
Ye Hejia et al., Development and Immune Efficacy of Recombinant Avian Influenza Inactivated Vaccine (H7N9 Subtype, Strain rGD76), Progress in Veterinary Medicine, vol. 40, No. 8, Dec. 31, 2019, p. 44-p. 48.
Li Bo, Sequence Analysis and Pathogenicity Study of a Novel Highly Pathogenic H7N9 Influenza Virus, College of Veterinary Medicine, South China Agricultural University, Jun. 2017.
Liao Ming, H5 subtype avian influenza virus is currently circulating in China, and the construction of its recombinant vaccine should achieve full coverage in terms of antigenicity, Northern Animal Husbandry, Issue 9, May 5, 2017.
Zhu Xuesong, South China Biology—an enterprise model combining industry,education and research, Enterprise Style, No. 4, Dec. 31, 2014, pp. 23-24.
Xue Suqiang et al., Inactivated Avian Influenza Vaccine for Waterfowl (H5N2 Subtype, D7 Strain), Northern Animal Husbandry, Issue 15, Aug. 5, 2013.
Zhang Jiahao et al., Evolution and Antigenic Drift of Influenza A (H7N9) Viruses, China, 2017-2019, Emerg Infect Dis., vol. 40, No. 8,Aug. 31, 2020.
E. Hoffmann et al. Universal primer set for the full-length amplification of all influenza A viruses,Arch Virol (2001) 146: 2775-2289.
Erich Hoffmann et al., Eight-plasmid system for rapid generation of influenza virus vaccines, Vaccine 20 (2002) 3165-3170.

* cited by examiner

*Primary Examiner* — Michael D Burkhart
(74) *Attorney, Agent, or Firm* — Yue (Robert) Xu; Apex Attorneys at Law, LLP

(57) ABSTRACT

The present disclosure discloses a whole avian-origin reverse genetic manipulation system and its use in producing a recombinant H7N9 avian influenza vaccine. The whole avian-origin reverse genetic manipulation system is an eight-plasmid reverse genetic manipulation system based on H5N2 subtype avian influenza D7 virus strain, which is comprised of 8 recombinant plasmids respectively containing PB2, PB1, PA, HA, NP, NA, M and NS gene fragments derived from H5N2 subtype avian influenza D7 virus strain. The genome of the recombinant H7N9 subtype avian influenza vaccine of the present disclosure is comprised of an NA gene and a modified HA gene derived from a highly pathogenic H7N9 subtype avian influenza virus strain, as well as PB2, PB1, PA, NP, M and NS genes derived from H5N2 subtype avian influenza D7 virus strain.

7 Claims, 5 Drawing Sheets
Specification includes a Sequence Listing.

FIG. 1

```
                CCTGAGGTTCCAAAGAGAAAACGGACTGCGAGAGGCCTATTT   SEQ ID NO: 21
LN155-wHA        P   E   V   P   K   R   K   R   T   A   R   G   L   F   SEQ ID NO: 20

LN155-rHA        P   E   V   P   K               R   G   L   F   SEQ ID NO: 22
```

WHOLE AVIAN-ORIGIN REVERSE GENETIC SYSTEM AND ITS USE IN PRODUCING H7N9 SUBTYPE AVIAN INFLUENZA VACCINE

CROSS REFERENCE TO RELATED APPLICATIONS

This application claims the priority of Chinese Patent Application No. 202110564096.4, filed on May 24, 2021, and the disclosure of which is hereby incorporated by reference.

FIELD

The present disclosure relates to the field of reverse genetics technology and animal infectious diseases, and specifically relates to a whole avian-origin reverse genetic manipulation system and its use in producing H7N9 avian influenza vaccine.

BACKGROUND

Avian influenza (AI) is an infection and/or disease syndrome caused by avian influenza virus (AIV), which seriously affects the development of poultry farming and threatens human health. Poultry can show different clinical symptoms after infection. According to the pathogenicity of the virus, it can be divided into low pathogenic avian influenza (LPAI) virus and highly pathogenic avian influenza (HPAI) virus. The low pathogenic H7N9 subtype avian influenza virus that appeared in 2013 was widely circulating in the poultry flocks and people in China, while in the second half of 2016, the highly pathogenic H7N9 subtype avian influenza variant appeared in Guangdong, and it spread and was circulating rapidly in farms and people. The H7N9 subtype avian influenza virus evolves and mutates rapidly, posing a great threat to animals and humans, and it is of great significance to quickly develop a protective avian influenza vaccine.

In order to meet the requirements of large-scale production and reduce losses due to insufficient vaccine supply or poor immunization effect, it is urgent to prepare vaccine strains with ideal immune protection effects. Therefore, it is necessary to modify the popular virus strains. In addition to maintaining the original immunogenicity and eliminating its pathogenic ability, the vaccine candidate strains are also required of improved virus titer during the chick embryo culture. The use of reverse genetics technology to construct avian influenza vaccine is currently the main technical means. In the prior art, recombinant avian influenza vaccine is constructed by utilizing human influenza vaccine as a backbone. (e.g., Hoffmann E, Krauss S, Perez D et al. Eight-plasmid system for rapid generation of influenza virus vaccines. *Vaccine*, 2002, 20:3165-3170). However, since the vaccine contains human genes, it may potentially cause the risk of recombinant avian influenza virus infecting humans.

SUMMARY

An object of the present disclosure is to overcome the above-mentioned shortcomings and deficiencies existing in the prior art, and to provide a whole avian-origin reverse genetic manipulation system.

The second object of the present disclosure is to provide use of the whole avian-origin reverse genetic manipulation system in the manufacture of H7N9 subtype avian influenza vaccine.

The third object of the present disclosure is to provide a recombinant H7N9 subtype avian influenza virus strain.

The above-mentioned objects of the present disclosure are achieved by the following technical solutions.

A whole avian-origin reverse genetic manipulation system (also referred to as D7 system) based on H5N2 subtype avian influenza D7 virus strain. The system is a reverse genetic manipulation system comprising 8 plasmids, and the 8 plasmids are respectively recombinant plasmids containing PB2, PB1, PA, HA, NP, NA, M and NS genes derived from H5N2 subtype avian influenza D7 virus strain; and the PB2, PB1, PA, HA, NP, NA, M and NS genes have nucleotide sequences set forth in SEQ ID NOs: 1-8, respectively.

The PB2, PB1, PA, HA, NP, NA, M and NS genes of the D7 virus strain encode the PB2 protein, PB1 protein, PA protein, HA protein, NP protein, NA protein, M1 protein (encoded by M gene), M2 protein (encoded by M gene), NS1 protein (encoded by NS gene), and NS2/NEP protein (encoded by NS gene). Among them, PB2 protein, PB1 protein, PA protein, NP protein, M1 protein and M2 protein, NS1 protein and NS2/NEP protein are internal proteins of the virus and are required for the formation of virus particles. HA protein and NA protein are glycoproteins on the surface. HA protein is the main protein that determines the pathogenicity and antigenicity of influenza virus. NA protein is a receptor-destroying enzyme (RDE), which can play a role of cleavage to release the progeny virus from the surface of host cells, and also presents certain antigenicity.

The H5N2 subtype avian influenza D7 strain is a virus strain isolated and developed by South China Agricultural University in 2013, and it was used to prepare the world's first whole avian-origin H5N2 subtype avian influenza inactivated vaccine for waterfowl. In the present disclosure, the avian influenza D7 virus strain, which is specially used for waterfowl and is highly adapted to chick embryos, is used to establish an eight-plasmid reverse genetic manipulation system (D7 system) based on the D7 strain for the development of avian influenza vaccines. All the gene fragments of the recombinant avian influenza virus rescued with the D7 system as the backbone are derived from poultry, which preserves the inherent interspecies barrier between avian influenza virus and human influenza virus, and reduces the risk of recombinant avian influenza vaccine infecting humans, fully meeting biosafety requirements.

The vector used in the D7 system is pSMC vector (modified from pCI vector of Promega), and the obtained recombinant plasmids are named pSMC-PB2, pSMC-PB1, pSMC-PA, pSMC-HA, pSMC-NP, pSMC-NA, pSMC-M and pSMC-NS, respectively.

Specifically, the pSMC vector is constructed by: removing BsmBI restriction enzyme site in pCI vector and introducing an Amp element (AmpR-promoter) to obtain pCI-NEW vector; synthesizing a nucleotide fragment containing transcriptional promoter and terminator sequences; performing double enzyme digestion on the pCI-NEW vector and the synthesized nucleotide fragment with XhoI and MluI, followed by ligation and transformation to obtain a recombinant plasmid; and performing enzyme digestion identification to obtain a positive plasmid as the successfully constructed pSMC vector.

The D7 system of the present disclosure can rapidly produce the H7N9 subtype avian influenza vaccine strain matched with the circulating H7N9 virus strain, which is of great significance for the prevention and control of highly pathogenic H7N9 subtype avian influenza.

The present disclosure also provides a recombinant H7N9 subtype avian influenza virus, wherein the genome of the recombinant virus is comprised of a modified HA gene and an NA gene derived from a highly pathogenic H7N9 subtype circulating avian influenza virus strain, as well as PB2, PB1, PA, NP, M and NS genes of D7 system; the modified HA gene has a sequence set forth in SEQ ID NO: 9, and the NA gene has a sequence set forth in SEQ ID NO: 10. The recombination of the six internal genes of the D7 system with the modified HA gene and the NA gene derived from a highly pathogenic H7N9 subtype circulating avian influenza virus strain in the form of "6+2" can rescue a recombinant virus, which is able to maintain good growth titer and antigenicity in chick embryos.

Preferably, the highly pathogenic H7N9 subtype circulating avian influenza virus strain is A/Chicken/Liaoning/19155/2019 (H7N9), abbreviated as LN155 strain.

The present disclosure also provides a method for producing the recombinant H7N9 subtype avian influenza virus strain, comprising recombining a modified HA gene and an NA gene derived from a highly pathogenic H7N9 subtype circulating avian influenza virus strain with PB2, PB1, PA, NP, M and NS genes of D7 system to obtain the recombinant virus.

Specifically, the method comprises: constructing plasmids respectively containing PB2, PB1, PA, NP, M and NS genes of D7 system; constructing plasmids respectively containing the modified HA gene with a sequence set forth in SEQ ID NO: 9 and the NA gene with a sequence set forth in SEQ ID NO: 10; and mixing the above 8 plasmids, mixing the mixed plasmids with a transfection reagent, adding to 293T cells and culturing the cells to obtain the recombinant H7N9 subtype avian influenza virus.

The present disclosure modifies the highly pathogenic H7N9 subtype avian influenza LN155 virus strain with the cleavage site of HA gene from PEVPKRKRTARGLF (SEQ ID NO: 20) to PEVPKGRGLF (SEQ ID NO: 22) to reduce its pathogenicity. Subsequently, NA gene and the HA gene modified with the cleavage site are recombined with the six internal genes of D7 system in the form of "6+2" and transfected into 293T cells to successfully generate the recombinant virus.

As a preferred embodiment, the present disclosure also provides a method for producing an H7N9 subtype avian influenza inactivated vaccine, which specifically comprises steps of:

(1) Construction of pSMC Vector for Reverse Genetic System

First, removing BsmBI restriction enzyme site in pCI vector (product of Promega) by PCR technique to obtain pCI-NEW vector; then synthesizing a DNA fragment containing transcription promoter (pol I promoter) and conventional transcription terminator sequences by gene synthesis; and finally, performing double enzyme digestion on the pCI-NEW vector and the obtained DNA fragment with XhoI and MluI, followed by ligation, transformation and identification to obtain a positive plasmid as pSMC vector.

(2) Construction and Identification of D7 Reverse Genetic System

Amplifying eight gene fragments (PB2, PB1, PA, HA, NP, NA, M, and NS) derived from the D7 virus strain respectively, and then ligating the fragment to the reverse genetic system vector pSMC, and the obtained positive plasmids are named pSMC-PB2, pSMC-PB1, pSMC-PA, pSMC-HA, pSMC-NP, pSMC-NA, pSMC-M and pSMC-NS respectively, that is to establish a reverse genetic system based on the D7 strain as an avian influenza vaccine development platform. Co-transfecting the above 8 plasmids into 293T cells, and 48 h later, inoculating the cell culture supernatant into 9~11-day-old SPF (specific-pathogen-free) chick embryos, and collecting the virus. After testing, the successfully rescued virus can be stably passaged in chick embryos. After sequencing identification, the reverse genetic system is successfully constructed.

(3) Amplification of HA and NA Gene Fragments of Recombinant Virus

Designing overlap primers based on the sequence of HA gene derived from the highly pathogenic avian influenza LN155 virus strain of H7 subtype in order to delete the cleavage site in the HA protein. Site-directly modifying the sequence of HA gene by the fusion PCR, and the modified fragment is named rHA. Meanwhile, amplifying the full-length sequence of NA gene with universal primers, and the fragment is named rNA. The rHA gene has a sequence set forth in SEQ ID NO: 9, and the rNA gene has a sequence set forth in SEQ ID NO: 10.

(4) Construction of Target Plasmids

Performing enzyme digestion with restriction endonuclease BsmBI followed by ligation to clone the rHA and rNA fragments into the pSMC expression vector, and the positive recombinant plasmids identified by sequencing are named pSMC-rHA and pSMC-rNA.

(5) Rescue of Recombinant Virus rLN155

Co-transfecting the recombinant plasmids pSMC-rHA and pSMC-rNA with pSMC-PB2, pSMC-PB1, pSMC-PA, pSMC-NP, pSMC-M and pSMC-NS of the D7 system into 293T cells. After 48 h, the transfected cells and supernatant is collected and inoculated into 9~11-day-old SPF chick embryos. After 60 h, detecting the hemagglutination activity, and harvesting the allantoic fluid with hemagglutination activity. After identification by PCR and sequencing, the obtained virus is the target recombinant virus rLN155, a recombinant H7N9 subtype avian influenza virus.

The present disclosure also provides a whole avian-derived H7N9 subtype avian influenza recombinant vaccine H71903 based on reverse genetic technology, comprising an immunizing amount of the above-mentioned H7N9 subtype avian influenza virus as an antigen. The vaccine can improve the cross-reactivity of the body to the highly pathogenic avian influenza circulating virus strain in recent years, can induce poultry to produce high-level antibodies, and shows a good protective effect, which provides an effective tool for the prevention and control of avian influenza.

The present disclosure also provides use of the H7N9 subtype avian influenza recombinant virus and the recombinant whole avian-origin H7N9 subtype avian influenza vaccine H71903 in the manufacture of a medicament for preventing and treating H7N9 subtype avian influenza.

Compared with the prior art, the present disclosure has the following beneficial effects.

(1) The present disclosure provides a whole avian-origin reverse genetic manipulation system (D7 system) based on the H5N2 subtype avian influenza D7 virus strain. All gene fragments of the system are derived from birds, which preserves the inherent interspecies barrier between avian influenza virus and human influenza virus, and reduces the risk of human infection. The system can rapidly produce the H7N9 subtype avian influenza vaccine strain matched with the circulating virus strain, which is of great significance for the prevention and control of highly pathogenic H7N9 subtype avian influenza. It is a safe and efficient whole avian-origin reverse genetics system.

(2) The present disclosure also provides an H7N9 subtype avian influenza virus strain, which is rescued by the recombination of D7 system with the modified HA gene and the NA gene derived from the highly pathogenic H7N9 subtype avian influenza circulating virus strain in the form of "6+2". The virus can maintain good titer and antigenicity during the chick embryo culture. Besides, the recombinant avian influenza virus constructed with the D7 strain as the backbone has no pathogenicity and fully meets the biological safety requirements. The vaccine H71903 prepared with the recombinant virus has excellent antigen matching and safety, can improve the body's cross-reactivity to the highly pathogenic avian influenza circulating virus strain in recent years, and can induce poultry to produce high levels of antibodies and good protection effects. Moreover, the vaccine can protect poultry from other highly pathogenic H7 subtype avian influenza viruses and provides an effective tool for the prevention and control of avian influenza.

BRIEF DESCRIPTION OF DRAWINGS

FIG. 1 is the construction flow chart and use of avian influenza vaccine strain H71903 in the present disclosure.

FIG. 6 is a comparison diagram of the cleavage site sequence of the modified rHA gene from the LN155 strain and the original sequence in the present disclosure.

FIG. 7 shows the survival rate of the immunized group and the control group of SPF chicken after virus challenge in the present disclosure.

DETAILED DESCRIPTION

The present disclosure is further described below in conjunction with the accompanying drawings and specific examples. However, the examples do not limit the present disclosure in any form. Unless otherwise specified, the reagents, methods and equipment used in the present disclosure are conventional reagents, methods and equipment in the technical field.

Unless otherwise specified, the reagents and materials used in the following examples are commercially available.

Polynucleotides encoding viral proteins can be synthesized artificially according to the sequences disclosed in the present invention, and commonly used promoters, transcription terminators, resistance genes, etc. can be synthesized according to the prior art.

The avian influenza virus strain A/Duck/Guangdong/D7/2007 (H5N2), referred to as the D7 strain or D7 virus strain, is isolated and preserved by the National and Regional Joint Engineering Laboratory for Medicament of Zoonoses Prevention and Control.

The highly pathogenic avian influenza virus strain A/Chicken/Liaoning/19155/2019 (H7N9), abbreviated as LN155 strain or LN155 virus strain, is isolated and preserved by the National and Regional Joint Engineering Laboratory for Medicament of Zoonoses Prevention and Control.

Figure 1:
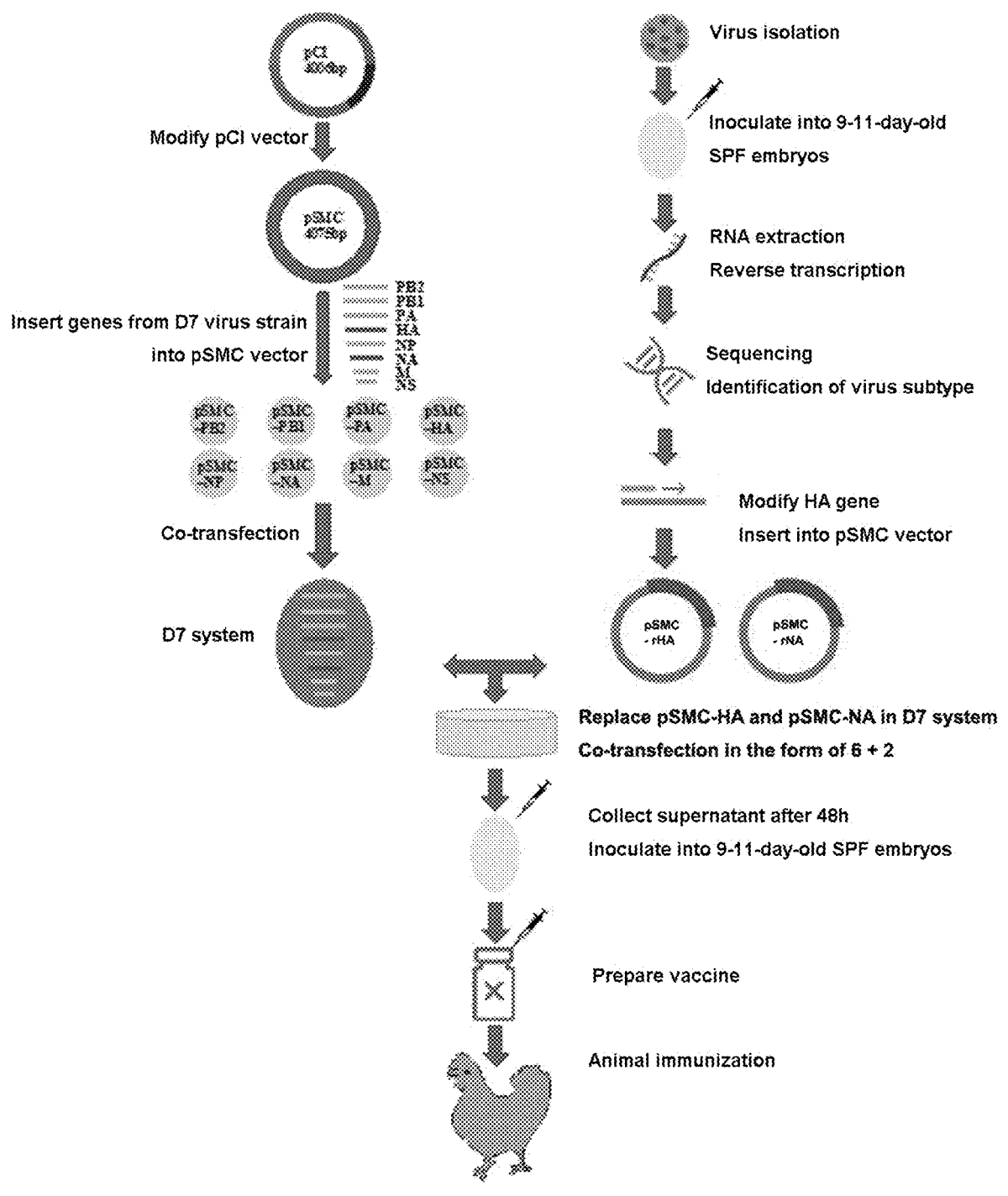

The construction flow chart and uses of the avian influenza vaccine candidate H71903 of the present disclosure are shown in FIG. 1, which specifically includes the following embodiments.

Deposit information: The recombinant H7N9 subtype avian influenza virus rLN155 was deposited under a deposit accession number of CCTCC NO: V202219 in the China Center for Type Culture Collection (Address: No. 299, Bayi Road, Wuchang District, Wuhan City, Hubei Province, China) on Mar. 8, 2022.

Figure 2:
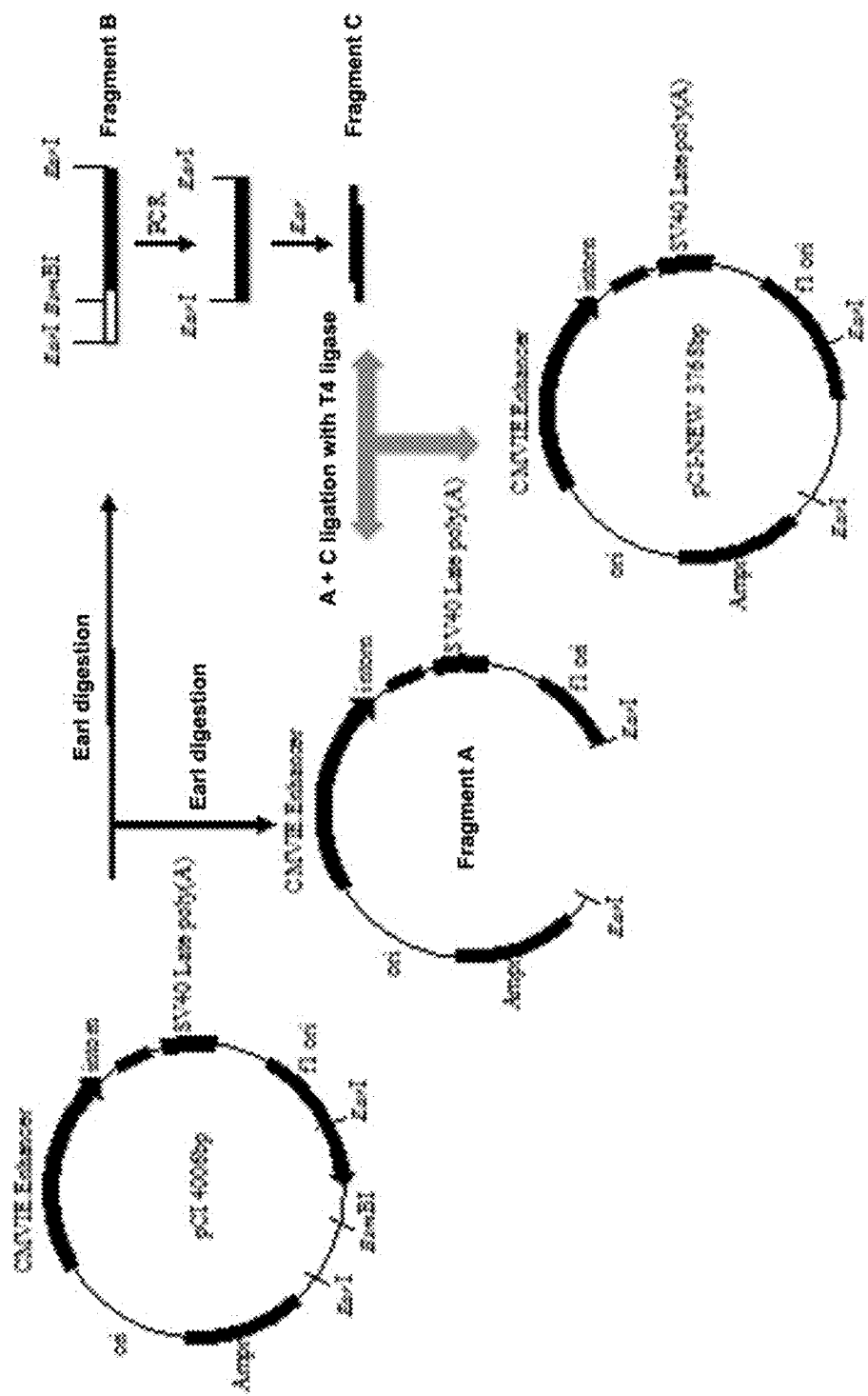
FIG. 2 is a schematic diagram of the construction of the pCI-NEW vector in the present disclosure.
Figure 3:
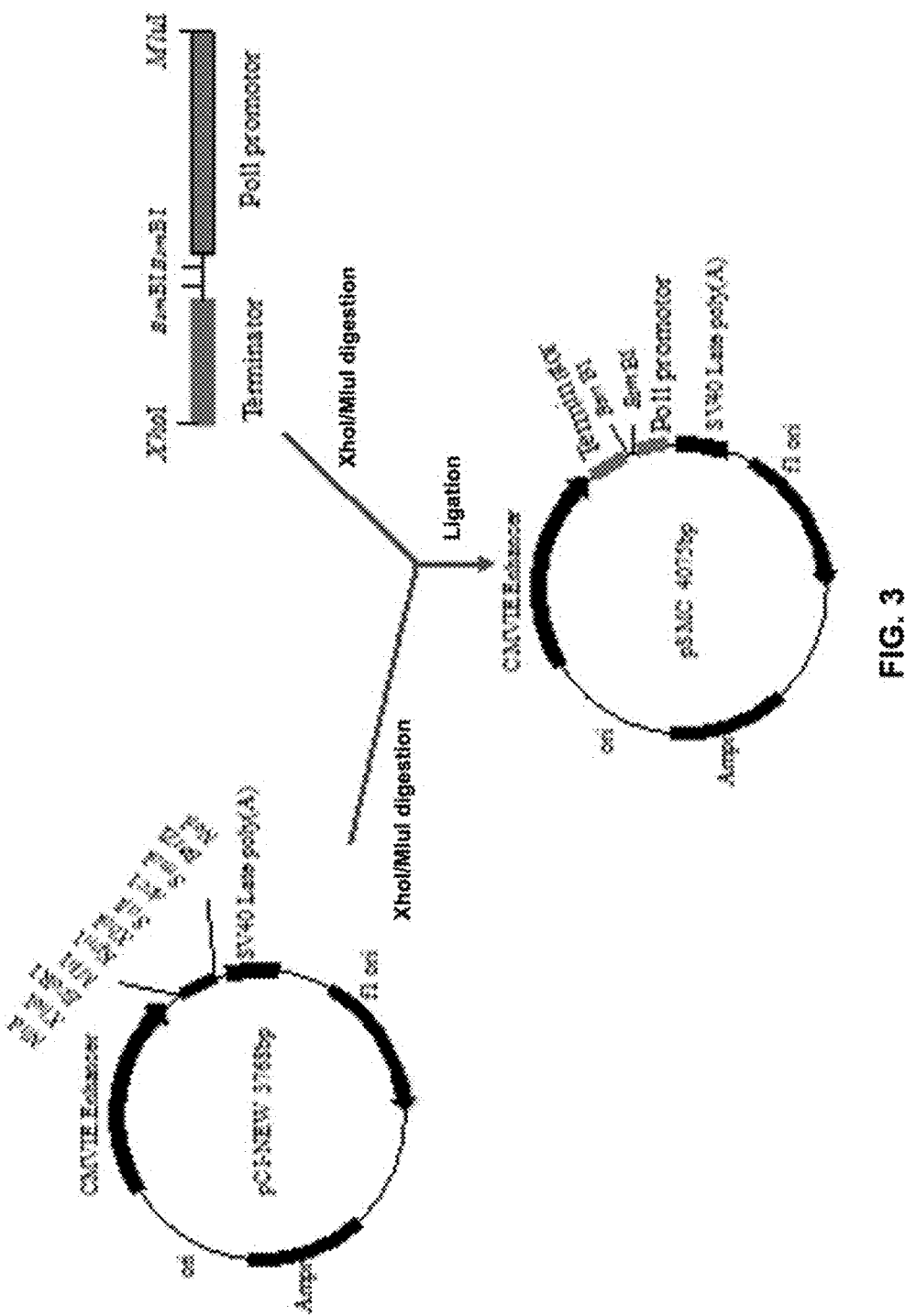
FIG. 3 is a schematic diagram of the construction of pSMC vector in the present disclosure.

Example 1 Construction of a Whole Avian-Origin Reverse Genetic Manipulation System Based on D7 Strain for Avian Influenza Vaccine 1. Construction of the Reverse Genetic System Vector pSMC (FIG. 2 and FIG. 3)

(1) Engineering of pCI Vector

The pCI vector was a product of Promega (Cat. No. BR180). In order to remove the BsmBI restriction enzyme site in the pCI vector plasmid, the pCI vector was digested with the restriction endonuclease EarI to obtain a long fragment A and a short fragment B. The amplification primers pCI-EarI-1 and pCI-EarI-2 were designed according to the sequence of short fragment B.

```
pCI-EarI-1:
                                    (SEQ ID NO: 11)
5'-TAGCGAGAGGCCGCACG-3';

pCI-EarI-2:
                                    (SEQ ID NO: 12)
5'-TCTTCGTTCGGTCACAGCTTCTGTAAG-3'.
```

Amplification was carried out using short fragment B as a template to obtain fragment C, which was recovered. Fragment C and fragment A were digested and recovered with EarI respectively, and then ligated. After transformation, bacteria picking and plasmid extraction, enzyme digestion with BsmBI and identification by sequencing was performed, and the plasmid verified to be correct was named as pCI-NEW vector.

(2) Acquisition of Transcription Elements

DNA fragments containing transcription elements (pol I promoter and common transcription terminator) were obtained by gene synthesis. The sequence of the terminator is

```
                                    (SEQ ID NO: 13)
CCAGGGTACTGGTCCTGACCACGTTGGAGGGGG GA.
```

(3) Enzyme Digestion of pCI-NEW Vector and DNA Fragments Containing Transcription Elements The pCI-NEW vector and the DNA fragment synthesized in step (2) were subjected to double digestion with XhoI and MluI.

(4) Ligation and Transformation of Digestion Products from pCI-NEW Vector and DNA Fragments Containing Transcription Elements The pCI-NEW vector and DNA fragments in step (3) were recovered, and subjected to ligation, transformation, bacteria picking, plasmid extraction, and enzyme digestion identification.

(5) Enzyme Digestion Identification

The plasmids extracted in step (4) were identified by single digestion with BsmBI and double digestion with XhoI and MluI, respectively.

(6) Sequencing Identification

The plasmids identified as positive by enzyme digestion in step (5) were sequenced, and the plasmid whose sequence was verified to be correct was named pSMC vector.

2. Construction of D7 System

Eight gene fragments of D7 strain (PB2, PB1, PA, HA, NP, NA, M and NS genes) were amplified by PCR with reference to universal primers of 8 gene sequences of influenza virus (Universal primer set for the full-length amplification of all influenza A viruses. Arch Virol. 2001 December; 146(12):2275-89). The 8 gene fragments derived from the D7 virus strain obtained by amplification were inserted into the reverse genetic vector pSMC according to the conventional molecular biology experiment method, and the obtained 8 plasmids were named pSMC-PB2, pSMC-PB1, pSMC-PA, pSMC-HA, pSMC-NP, pSMC-NA, pSMC-M and pSMC-NS. A D7 reverse genetic system vaccine development platform was established to provide the required genes for vaccine strains. After 8 plasmids were co-transfected into 293T cells, the H5N2 avian influenza virus with hemagglutination activity could be successfully assembled, and could be stably passaged on chick embryos. After sequencing identification, it was proved that the reverse genetic system was successfully constructed.

Example 2 Construction of Recombinant H7N9 Subtype Avian Influenza Virus

1. Extraction and Reverse Transcription of Viral RNA

Total RNA from virus-containing allantoic fluid was extracted using a total RNA extraction kit. cDNA was obtained by reverse transcription according to the instructions of M-MLV reverse transcriptase.

2. Design of Primers

The full-length primers of HA and NA fragments for amplification were designed based on the HA and NA gene sequences of LN155 strain. Overlap primers for modifying the cleavage site of the HA gene were designed based on the HA sequence. The specific sequence is as follows, and the recognition sequence of the restriction endonuclease BsmBI is underlined.

```
LN155-HA1-F:
                                       (SEQ ID NO: 14)
5'-TGAGGTTCCAAAGGGAAGAGGCCTATTTGGTGCTATAGC-3'

LN155-HA2-R:
                                       (SEQ ID NO: 15)
5'-AAATAGGCCTCTTCCCTTTGGAACCTCAGGAACATTCTTC-3'

Bm-HA-1F:
                                       (SEQ ID NO: 16)
5'-TATTCGTCTCAGGGAGCAAAAGCAGGGG-3'

Bm-NS-890R:
                                       (SEQ ID NO: 17)
5'-ATATCGTCTCGTATTAGTAGAAACAAGGGTGTTTT-3'

Bm-NA-1F:
                                       (SEQ ID NO: 18)
5'-TATTCGTCTCAGGGAGCAAAAGCAGGAGT-3'

Bm-NA-1413R:
                                       (SEQ ID NO: 19)
5'-ATATCGTCTCGTATTAGTAGAAACAAGGAGTTTTTT-3'
```

3. Modification of HA Fragments and Amplification and Purification of HA and NA Fragments Fragmented PCR amplification and fusion PCR amplification were performed on the HA fragment of LN155 strain using high-fidelity DNA polymerase and fragmented primers, and the full-length sequence of NA gene was amplified.

Figure 4:
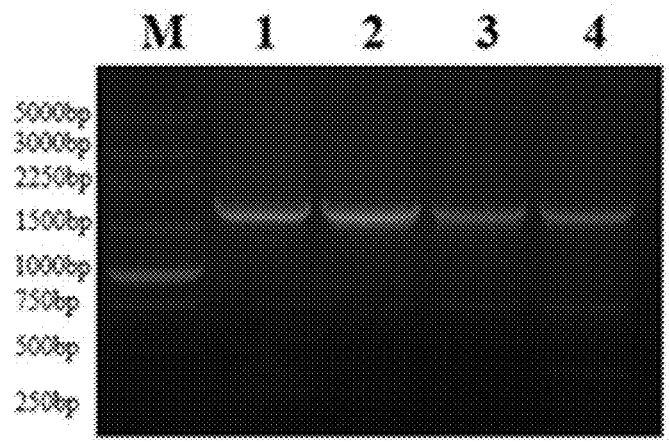
FIG. 4 is the results of PCR amplification of the HA gene of the donor virus strain and the modified HA gene in the present disclosure. Lanes 1 and 2 are the modified HA gene, lanes 3 and 4 are the HA gene of the donor virus strain; and M is the 250 bp DNA Ladder.
Figure 5:
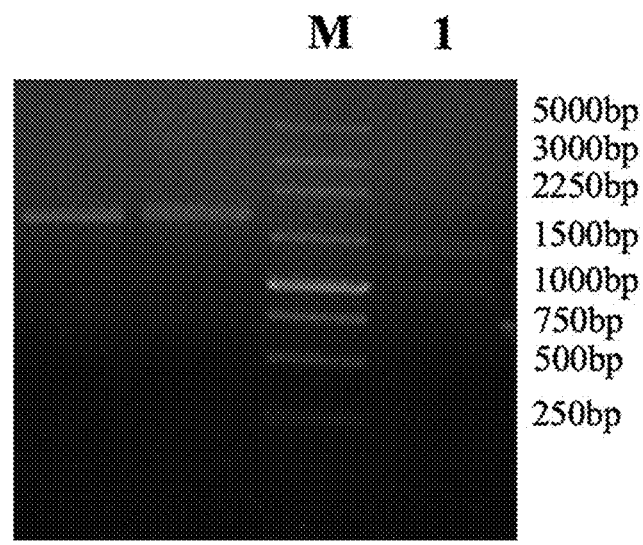
FIG. 5 is the results of PCR amplification of the NA gene of the donor LN155 virus strain in the present disclosure. Lane 1 is the NA gene of the donor virus strain; and M is the 250 bp DNA Ladder.

The upstream and downstream universal primers with BsmBI restriction sites were paired with segmented primers, respectively, and two fragments, HA1 and HA2, were amplified. Finally, fusion PCR was performed to amplify the complete modified HA fragment. NA fragment was amplified. After PCR amplification, the amplified products were preliminarily detected by 1% agarose gel electrophoresis (the amplification results are shown in FIG. 4 and FIG. 5, respectively), and the modified HA gene fragment and the NA gene fragment that were successfully amplified were cut off and named rHA and rNA, respectively. The rHA was identified by sequencing and then compared with the original sequence, and it was confirmed that the cleavage site had been successfully modified (as shown in FIG. 6). The nucleotide sequences of rHA and rNA are shown in SEQ ID NO: 9 and SEQ ID NO: 10, respectively.

4. Construction, Screening and Purification of Target Plasmids

The amplified target fragments rHA, rNA and pSMC expression vector were digested with restriction endonuclease BsmBI, respectively (55° C. water bath for 3 h).

The digested products were recovered, ligated and transformed into DH5α competent cells, which were cultured at 37° C. overnight, and the positive clones were initially screened by PCR (bacteria suspension as template). The specific operation is as follows: a single colony was picked out and transferred into an EP tube containing 500 µL of LB medium (ampicillin-resistant), which was then placed on a shaker at 37° C. and cultured with shaking for 3-4 h. 2 µL of bacterial suspension was used for PCR amplification, and 10 µL of PCR product was subjected to electrophoresis detection. The PCR-positive clones were identified by sequencing. The clones with correct sequencing were further expanded and cultured, and the plasmids were extracted. The concentration and purity of the plasmids were determined, and stored at −40° C. for future use.

5. Rescue and Identification of Recombinant Virus rLN155

Cell preparation. One day before transfection, 293T cells were digested with trypsin and counted. Cells of appropriate concentration were added to a 12-well cell culture plate, which was then placed in a 37° C. incubator containing 5% $CO_2$. The cells were used for subsequent experiments when the cell density reached about 90%.

Transfection. Eight plasmids (300 ng/plasmid) required for transfection were added into EP tubes containing 150 µL serum-free medium Opti-MEM, mixed well, and named as solution A; 4.8 µL Lipofectamine 2000 (Invitrogen) was added to another EP tube containing 150 µL of Opti-MEM, named solution B, mixed well, and allowed to stand at room temperature for 5 min. Solution A was added to solution B, mixed gently and allowed to stand for 20 min. The 12-well culture plate with 293T cells was taken out, and the original medium was discarded. The plate was then washed twice with sterilized PBS, the mixture of plasmid and liposome was added, and the plate was placed in a 37° C. incubator with 5% $CO_2$ for 4-6 h of culture. Then the DMEM medium containing BSA (concentration of 0.2%) was used to replace the medium containing Lipofectamine 2000 to continue the culture. After 48 h, the supernatant and cells were collected, mixed well and inoculated to 9~11-day-old SPF embryos. After 60 h of inoculation, the allantoic fluid was tested for hemagglutination activity. The presence of hemagglutination activity indicated that it contained influenza virus. Allantoic fluid with hemagglutination activity was harvested and sequenced to identify the virus sequence. The virus was continuously passaged for five generations, and after collection, it was aliquoted and stored at −80° C. for future use.

Identification of the recombinant virus. The RNA of the successfully rescued virus was extracted and subjected to whole genome sequencing by RT-PCR. After verification, the obtained recombinant virus was named rLN155.

Example 3 Preparation of vaccine H71903 with recombinant virus rLN155

Example 3 Preparation of vaccine H71903 with recombinant virus rLN155

1. Preparation of Vaccine

Large-scale preparation of antigens. The rLN155 virus used for vaccine preparation was diluted to about $10^{-4}$ $TCID_{50}/mL$ using sterile DMEM cell culture medium, and the diluted virus was inoculated to allantoic cavity of 9~11-day-old SPF chick embryos at 0.2 mL/embryo under sterile conditions, sealed and placed in a 37° C. incubator. After 60 h of incubation, chick embryo allantoic fluid was collected in a biological safety cabin, and the hemagglutination (HA) titer was determined.

Antigen inactivation: The virus solution collected above was inactivated with a final concentration of 0.1% formaldehyde, sealed, placed in a shaker, and incubated at 37° C. for 24 h; then the inactivated virus was inoculated to 9~11-day-old SPF chick embryos at 0.2 mL/embryo.

After culture at 37° C. for 48 h, the hemagglutination titer was tested to verify whether the virus had been completely inactivated.

Preparation of inactivated oil emulsion vaccine H71903. Preparation of water phase: 97 parts of the solution containing the inactivated rLN155 virus and 3 parts of Tween-80 were mixed well. Preparation of oil phase: 94 parts of Marcol-52 white mineral oil and 6 parts of Span-80 were mixed well and sterilized by autoclaving for future use. The oil phase and the water phase in a ratio of 2:1 were emulsified using an emulsifier at 25,000 r/min for 5 min. During the mixing, a few drops of the prepared inactivated vaccine can be placed on the surface of cold water. In the case that only the first drop diffused and the others did not, the formulation is judged to be water-in-oil. The prepared vaccine was then put into a centrifuge to centrifuge at 3,000 r/min for 15 min, and the presence of stratification was observed. If absent, the preparation was successful. The vaccine, named H71903, was aliquoted and stored at 4° C.

2. Serum Hemagglutination Inhibition Test (HI test) for Cross-Reactivity

SPF chickens were immunized with H71903 vaccine and commercial inactivated vaccine rGD76 for H7 subtype avian influenza, respectively. After 21 days, serum was collected, and was subjected to serum HI test with 12 virus strains from 2016 to 2019 for cross-reactivity (see Table 1). The results show that compared with rGD76, H71903 vaccine had higher overall HI titer and better responsiveness to circulating virus strains.

TABLE 1

HI (log2) cross-test results

| Antigen (virus isolation time) | Serum H71903 | Serum rGD76 |
|---|---|---|
| LN155 (2019) | 9 | 7 |
| GD76 (2016) | 9 | 9 |

TABLE 1-continued

HI (log2) cross-test results

| Antigen (virus isolation time) | Serum H71903 | Serum rGD76 |
|---|---|---|
| 16044(2016) | 8 | 8 |
| 17178 (2017) | 7 | 6 |
| 17213 (2017) | 7 | 6 |
| SX1801 (2018) | 8 | 7 |
| HeB1908 (2019) | 8 | 5 |
| LN19010 (2019) | 9 | 7 |
| HeB1907 (2019) | 9 | 6 |
| LN (2019) | 10 | 7 |
| 19201(2019) | 9 | 6 |
| 19254 (2019) | 9 | 6 |

3. Immune Challenge Protection Test of H71903 Vaccine Strain in SPF Chicken

In order to verify the immune effect of H71903 vaccine strain, in this experiment, SD1115, LN155, HeB1908 and LN virus strains (SD1115 is H7N2 subtype strain, and the other three are H7N9 subtype virus strains) were diluted to 100 $LD_{50}$ as A/B/C/D treatment groups; and control groups (5 control chickens) were set up, named SD1115-control, LN155-control, HeB1908-control and LN-control. The chickens immunized with H71903 vaccine were challenged with SD1115, LN155, HeB1908 and LN virus by intranasal inoculation, 0.2 mL/chicken. After challenge, the chickens were observed in isolators for 14 consecutive days. On Day 5 after infection, the throat and cloacal swabs of chickens were collected, determined for the hemagglutination titer and analyzed for virus content.

(1) HI Antibody Titer of Serum from Immunized Chicken

On Day 21 of immunization, the blood of all the chickens in the treatment group and the control group in the isolator was collected and the serum was separated. The LN155 virus was used as the antigen to carry out the HI test. The HI antibody titers of the test chickens in each group are shown in Table 2. The results show that the HI neutralization titers of the four treatment groups A, B, C and D were all at high levels, and the geometric mean titer (GMT) of antibodies were 7.5, 7.5, 7.0 and 7.5, respectively.

TABLE 2

HI antibody titers of test chicken in each group (log2)

| Group | 1 | 2 | 3 | 4 | 5 | 6 | 7 | 8 | 9 | 10 | GMT |
|---|---|---|---|---|---|---|---|---|---|---|---|
| Group A | 8 | 8 | 8 | 7 | 7 | 8 | 8 | 7 | 6 | 8 | 7.5 |
| Group B | 8 | 8 | 7 | 7 | 8 | 7 | 7 | 8 | 8 | 7 | 7.5 |
| Group C | 6 | 7 | 6 | 8 | 8 | 6 | 7 | 8 | 8 | 8 | 7.0 |
| Group D | 8 | 8 | 7 | 8 | 7 | 8 | 7 | 7 | 7 | 8 | 7.5 |
| Control group | 0 | 0 | 0 | 0 | 0 | | | | | | |

(2) Survival Rate of SPF Chickens After Infection

The immunized chickens and the control chickens were challenged with virus at an amount of 100 $LD_{50}$, and the state of the chickens was observed and recorded for 14 consecutive days. All four groups of test chickens survived, while unimmunized control chickens developed depression and loss of appetite on Day 2 or Day 3, and died around Day 5. This result indicates that chickens were protected after immunization with recombinant inactivated vaccine H71903 (FIG. 7).

(3) Virus Detection of Throat/Anal Swabs of SPF Chickens After Infection

On Day 5 after challenge, the throat swabs and cloacal swabs of chickens in all treatment groups and control groups were collected and tested for virus content. As can be seen from Table 3, the four groups of immunized chickens had no virus detected after 5 days of challenge, indicating that the vaccine can protect the chickens from the lethal challenge of the highly pathogenic H7 subtype avian influenza virus. In contrast, all chickens in the control group died on Day 3 to Day 6, and the virus could also be detected in the swabs of live chickens collected on Day 5.

TABLE 3

Virus detection of immunized chickens

| Group | | Test Chicken No. | | | | | | | | | |
|---|---|---|---|---|---|---|---|---|---|---|---|
| A | Throat/anal swabs | 361 | 362 | 363 | 364 | 365 | 366 | 367 | 368 | 369 | 370 |
| | Detection result | − | − | − | − | − | − | − | − | − | − |
| B | Throat/anal swabs | 1 | 2 | 3 | 4 | 5 | 6 | 7 | 8 | 9 | 10 |
| | Detection result | − | − | − | − | − | − | − | − | − | − |
| C | Throat/anal swabs | 411 | 412 | 413 | 414 | 415 | 416 | 417 | 418 | 419 | 420 |
| | Detection result | − | − | − | − | − | − | − | − | − | − |
| D | Throat/anal swabs | 221 | 222 | 223 | 224 | 225 | 226 | 227 | 228 | 229 | 230 |
| | Detection result | − | − | − | − | − | − | − | − | − | − |

Note:
"+" means positive virus isolation,
"−" means negative virus isolation.

The test results of the recombinant avian influenza inactivated vaccine strain H71903 show that the vaccine had a good immune effect on SPF chickens aged 21 days that it not only induced high antibody levels in the immunized chickens, but also protected them from challenges of other highly pathogenic H7 subtype avian influenza virus with a protection rate up to 100% (FIG. 7).

The above-mentioned embodiments are preferred embodiments of the present disclosure, but the embodiments of the present disclosure are not limited by the above-mentioned embodiments. Any other changes, modifications, substitutions, combinations, and simplifications that do not depart from the spirit and principle of the present disclosure should be equivalent embodiments and are included within the protection scope of the present disclosure.

The invention claimed is:

1. A recombinant H7N9 subtype avian influenza virus, wherein the genome of the recombinant virus is comprised of an NA gene and a modified HA gene derived from a highly pathogenic H7N9 subtype avian influenza virus strain, as well as PB2, PB1, PA, NP, M and NS genes derived from H5N2 subtype avian influenza D7 virus strain; the modified HA gene has a sequence set forth in SEQ ID NO: 9, and the NA gene has a sequence set forth in SEQ ID NO: 10; the PB2, PB1, PA, NP, M and NS genes derived from D7 strain have nucleotide sequences set forth in SEQ ID NOs: 1-3, 5 and 7-8, respectively; the highly pathogenic H7N9 subtype avian influenza virus strain is A/Chicken/Liaoning/ 19155/2019; and the recombinant virus has a deposit accession number of CCTCC NO: V202219.

2. A method for producing the recombinant virus according to claim 1, comprising recombining an NA gene and a modified HA gene derived from a highly pathogenic H7N9 subtype avian influenza virus strain with PB2, PB1, PA, NP, M and NS genes derived from H5N2 subtype avian influenza D7 virus strain to obtain the recombinant virus.

3. The method according to claim 2 comprising:
constructing 6 plasmids expressing a protein encoded by PB2, PB1, PA, NP, M and NS genes derived from D7 virus strain, respectively,
constructing 2 plasmids respectively expressing a modified HA protein encoded by SEQ ID NO: 9 and an NA protein encoded by SEQ ID NO: 10; and
mixing the above 8 plasmids, mixing the mixed plasmids with a transfection reagent, and then adding to 293T cells to obtain the recombinant H7N9 subtype avian influenza virus.

4. The method according to claim 2, wherein the method comprises steps of:
S1 constructing an 8-plasmid reverse genetic manipulation system, the 8 plasmids respectively contain PB2, PB1, PA, HA, NP, NA, M and NS genes derived from H5N2 subtype avian influenza D7 virus strain, and the PB2, PB1, PA, HA, NP, NA, M and NS genes have nucleotide sequences set forth in SEQ ID NOs: 1-8, respectively;
S2. constructing 2 plasmids respectively containing the modified HA gene with a sequence set forth in SEQ ID NO: 9 and the NA gene with a sequence set forth in SEQ ID NO: 10; and
S3. mixing 6 plasmids respectively containing PB2, PB1, PA, NP, M and NS genes in step S1 with the 2 plasmids respectively containing the modified HA gene and the NA gene in step S2, mixing the mixed plasmids with the transfection reagent and adding to 293T cells, and culturing the cells to obtain the recombinant H7N9 subtype avian influenza virus.

5. The method according to claim 4, wherein a vector used for constructing the plasmid in step S1 is a pSMC vector, and the obtained 8 plasmids are pSMC-PB2, pSMC-PB1, pSMC-PA, pSMC-HA, pSMC-NP, pSMC-NA, pSMC-M and pSMC-NS, respectively.

6. The method according to claim 5, wherein the pSMC vector is constructed by:
   removing BsmBI restriction enzyme site in pCI vector to obtain pCI-NEW vector;
   synthesizing a nucleotide fragment containing transcriptional promoter sequence and transcriptional terminator sequence;
   performing double enzyme digestion on the pCI-NEW vector and the synthesized fragment with XhoI and MluI, followed by ligation and transformation to obtain a recombinant plasmid; and
   performing enzyme digestion identification and sequencing identification on the obtained recombinant plasmid to obtain a positive plasmid as the pSMC vector.

7. A method for preventing H7N9 subtype avian influenza, comprising administering to a subject in need thereof the recombinant H7N9 subtype avian influenza virus according to claim 1.

* * * * *

SEQUENCE LISTING

```
<160> NUMBER OF SEQ ID NOS: 22

<210> SEQ ID NO 1
<211> LENGTH: 2280
<212> TYPE: DNA
<213> ORGANISM: Artificial Sequence
<220> FEATURE:
<223> OTHER INFORMATION: Synthesized PB2 gene nucleotide sequence

<400> SEQUENCE: 1
atggagagaa taaagaatt aagagagcta atgtcgcaat cccgcacctg cgagatacta      60
acaaaaacca ctgtggacca tatggccata attaagaaat acacatcagg aagacaagag     120
aagaaccctg ctctcagaat gaaatggatg atggcaatga aatatccaat caccgcaaac     180
aagagaataa tggagatgat tcctgaaagg aatgaacaag gacagacgct gtggagcaag     240
acaaatgatg ctggatcgga cagggtaatg gtgtctcccc tagccgtaac atggtggaac     300
aggaatgggc cgacaacaag tacagtccat tatccaaaag tttacaaaac atactttgag     360
aaagttgaaa ggttaaaaca tggaacattt ggtcccgttc atttccgaaa ccaagttaaa     420
atacgccgcc gagttgatgt aaacccgggt catgcagatc tcagtgctaa agaagcacaa     480
gatgtcatca tggaggtagt tttcacaaat gaagtgggag ctagaatatt gacatcagaa     540
tcgcaattag caataacaaa agagaagaaa gaagagctcc aggattgtaa gattgctcct     600
ttaatggtgg cttacatgtt ggaaagggaa ctagttcgga aaactaggtt cctaccagta     660
tcaggcggga caagtagtgt gtacattgag gtattgcact tgactcaggg tacctgctgg     720
gaacagatgt acaccccggg cggagaagtg agaaatgatg atgttgacca gagtttgatc     780
attgctgcta gaaacattgt taggagagca acagtatcag ctgatccact gctatcacta     840
ttggagatgt gccacagcac acagatcggt gggataagga tggtggacat tctcaggcaa     900
```

-continued

```
aatccaactg aggagcaagc tgtggatata tgcaaagcag caatgggtct gagaatcagt    960
tcgtctttta gctttggagg cttcactttc aaaagaacaa gtggatcgtc tgtaaagaaa   1020
gaagaagaag tgcttacagg caacctccaa acattgagga ttagaataca tgaggggtat   1080
gaggagttca caatggttgg acggagggca acagctatcc tgaggaaagc aactagaagg   1140
ctgattcagt tgatagtaag tggaagagat gaacaatcaa ttgctgaagc aattattgta   1200
gcaatggtgt tctcacagga ggagtgtatg ataaaggcag tccgtggcga tttgaatttt   1260
gtaaacagag caaaccaaag attgaacccc atgcatcaac tcctgaggca cttccaaaag   1320
gatgcaaaag tgctatttca gaactgggga attgaaccca ttgacaatgt catggggatg   1380
atcggaatat tacccgatat gactccaagc acagagatgt cactgagagg ggtgagagtt   1440
agtaagatgg gagtggatga atattccagc actgagaggg tgactgtgag cattgaccgt   1500
ttcttaaggg tccgagatca gctggggaac atactactat ctcccgaaga agtgagtgaa   1560
acacagggaa cagagaaatt gacgataaca tattcatcat caatgatgtg ggaaatcaat   1620
ggtcctgagt cagtacttgt taacacctat caatggatca tcagaaattg ggagaccgtt   1680
aagattcaat ggtctcaaga ccctactatg ttgtacaata aaatggagtt tgaaccgttc   1740
caatccctgg tacccaaagc tgccagaagt ctatacagtg gatttgtgag aacactattc   1800
caacaaatgc gtgatatact gggaacattt gataccgttc aaataataaa gctgctacca   1860
tttgcagcag ccccaccgga gcagagcaga atgcagtttt cttccctaac tgtaaatgtg   1920
agaggctcag gaatgagaat actcgtaagg ggtaactccc ctgtgttcaa ttacaataag   1980
gtaaccaaaa ggcttacagt actcggaaag gatgcagggg cactgacaga agatccagat   2040
gagggaacag ccggagtgga gtctgcggta ctaaggggat tcttaattct aggcaaggag   2100
gacagaagat atggaccagc attaagcatc agtgaactga gcaatcttgc gaaaggggag   2160
aaagctaatg tgctgatagg gcaaggagac gtagtgttgg taatgaaacg gaaacgggac   2220
tctagcatac ttactgacag ccagacagcg accaaaagga ttcggatggc catcaattag   2280
```

```

<210> SEQ ID NO 2
<211> LENGTH: 2274
<212> TYPE: DNA
<213> ORGANISM: Artificial Sequence
<220> FEATURE:
<223> OTHER INFORMATION: Synthesized PB1 gene nucleotide sequence

<400> SEQUENCE: 2
atggatgtca atccgactct acttttcttg aaagtgccag tgcaaaatgc tataagtacc     60
acattccctt atactggaga tcctccatac agccatggaa caggaacagg atacaccatg    120
gacacggtca acagaacaca tcaatactca gaaaagggga aatggacaac aaacacagaa    180
actaaagcac cccaactcaa cccgattgac gggccgttgc ctgatgataa tgaaccgagc    240
gggtacgcac aaacggactg cgtgttggaa gcaatggctt tcctggaaga atcacaccca    300
gggattttcg aaaactcgtg tcttgaaaca atggaagttg ttcagcaaac aagagtggat    360
aaactaaccc aaggtcgcca gacctatgac tggacattga atagaaatca gccggctgct    420
actgcattgg ccaacaccat agaggtcttc agatcgaacg gtctaacagc taatgaatca    480
gggaggctaa tagatttcct aaaggacgtg acggactcaa tgaataaaga ggaaatggaa    540
ataacgaaac atttccagag aaagagaaga gtaagggaca acatgaccaa gaaaatggtc    600
acacaaagaa caatagggaa gaagaagcag aggctgaaca ggaggagcta tttaataaga    660
gcactgacac tgaacacaat gacaaaagat gcagaaagag gcaaattgaa aaggagggca    720
```

```
attgcaacgc ccggaatgca gatcagagga ttcgtgtact ttgtcgaaac actagcaagg    780
agcatttgtg agaaacttga gcaatctgga ctcccagttg gagggaacga gaagaaggct    840
aaactggcaa acgtcgtgag aaagatgatg actaactcac aagatacaga gctctccttt    900
acaattactg gggacaacac caaatggaat gagaatcaga atcctagagt gtttctagcg    960
atgataacat atattacaag aaatcaacct gaatggttta gaaatgtctt gagtattgct   1020
cctataatgt tctcaaacaa aatggcgaga ttagggaaag ggtacatgtt cgaaagcaag   1080
agcatgaagc tacggacaca agtaccagca gaaatgcttg caaccattga cctgaaatac   1140
ttcaatgaat caacgagaaa gaaaatcgag aaaataagac ctcttctaat agagggcaca   1200
gcctcattga gtcctggaat gatgatgggc atgttcaaca tgctgagtac ggtcttagga   1260
gtttcaatcc tgaatcttgg gcaaaagagg tacaccaaaa ccacatactg gtgggacgga   1320
ctccaatcct ctgatgattt cgccctaata gtgaatgcac caaatcatga gggaatacaa   1380
gctggggtag ataggttcta taggacctgc aaactagttg gaatcaatat gagcaaaaag   1440
aagtcttata taaataggac aggaacattt gagttcacaa gtttttttcta ccgttatgga   1500
tttgtggcca acttcagtat ggagctgccc agctttggag tgtctgggat caatgaatcg   1560
gctgacatga gcattggggt tacagtaata aagaacaata tgataaataa tgaccttgga   1620
ccagcaacag cccagatggc tcttcagcta ttcatcaagg attatcgata cacgtaccga   1680
tgccacaggg gtgatacgca aattcaaaca aggagatcat ttgagctgaa gaagctgtgg   1740
gagcagaccc gttcgaaggc aggattgttg gtctcagatg gagggccaaa tctatacaac   1800
atccggaatc tccacattcc agaggtctgc ttgaaatggg aattaatgga tgaggattat   1860
cagggcaggc tgtgcaatcc tctgaatccg tttgtcagtc ataaggagat tgagtcggta   1920
aacaatgccg tagtaatgcc agcccatggt ccagcaaaga gcatggaata tgatgccgtt   1980
gcaactacac actcatggat tcctaagagg aaccgttcca ttctcaatac cagccaaagg   2040
ggaattcttg aggatgaaca gatgtatcag aagtgctgca atctatttga gaaattcttc   2100
cctagtagtt catataggag gccagttgga atctctagca tggtggaggc catggtgtcc   2160
agggcccgaa ttgacgcacg aattgacttc gagtctggaa ggattaagaa agaagagttt   2220
gccgagatca cgaagatctg ttccaccatt gaagagctca gacggcaaaa atag         2274
```

```

<210> SEQ ID NO 3
<211> LENGTH: 2151
<212> TYPE: DNA
<213> ORGANISM: Artificial Sequence
<220> FEATURE:
<223> OTHER INFORMATION: Synthesized PA gene nucleotide sequence

<400> SEQUENCE: 3
atggaagact ttgtgcgaca atgcttcaat ccaatgatcg tcgagcttgc ggaaaaggca     60
atgaaagagt atggggaaga tccgaaaatc gaaacgaaca agtttgcggc aatatgcacc    120
catttggaag tctgcttcat gtattcagat ttccatttca ttgacgaaag aggcgaatca    180
ataattgtgg aatttggtga tccaaatgta ctattgaaac accgatttga aataattgaa    240
ggaagagacc ggacaatggc atggacagta gtgaatagca tctgtaacac cacaggagtc    300
gaaaaaccta aataccttcc agatctgtat gattacaagg ataaccgatt cattgagatt    360
ggagtgacac ggagggaagt tcacatatac tatctagaaa aggccaacaa gatgaaatcc    420
gagagaacac atattcacat cttctcattt acaggagaag aaatggccac caaagcggat    480
```

| | |
|---|---|
| tataccettg atgaagagag cagggcaagg atcaaaacta gactgttcac cataagacag | 540 |
| gaactggcta gcaggggtct atgggattcc tttcgccagt ctgagagagg cgaagagaca | 600 |
| attgaagaaa gatttgaaat cacaggaaca atgcgcaggc ttgccgacca aagtctccca | 660 |
| ccgaatttct ccagccttga aaactttaga gcctatgtgg atggattcga accgaacggc | 720 |
| tgcattgagg gcaagctttc tcagatgtca aaagaagtga ctgccagaat tgagcccttt | 780 |
| cttaagacaa caccacgtcc tctcagattg ccggatggac ctccctgttc caaaggtca | 840 |
| aaattcttac tgatggatgc tttgaaatta agcattgagg cccgagtca tgagggagag | 900 |
| gggataccgc tgtatgatgc gatcaaatgc atgaaaacat ttttcggctg aaagagccc | 960 |
| aaaattatca atcacatga agggtata acccaaatt atctcctagc ttggaagcag | 1020 |
| gtgctggcag agctccagga cattgaaaat gaggaaaaga tcccaaaaac gaagaacatg | 1080 |
| aagaaaacaa gccaattaaa gtgggcatta ggtgagaaca tggcaccaga aaaagtggac | 1140 |
| tttgaggatt gcaaagatgt tagtgacctg aaacaatatg acagtgatga gccggagccc | 1200 |
| aaatcgctag caagttggat ccaaagtgaa tttaacaaag catgtgagct gaccgattca | 1260 |
| agctgggtag aacttgatga aataggggaa gatgttgccc caatcgagca cattgcgagt | 1320 |
| atgagaagga attacttcac agcagaagtg tcgcactgcc gggctaccga gtatataatg | 1380 |
| aagggagtgt acataaatac agcattgctc aatgcatctt gtgcagccat ggatgacttc | 1440 |
| caattgattc caatgataag caaatgcaga acaaagaag ggagacggaa acaaacctg | 1500 |
| tatgggttca ttatcaaggg aaggtcccat ttgaggaatg atactgatgt ggtaaacttt | 1560 |
| gtgagcatgg aatttctct tacagacccg aggcttgaac cacacaaatg ggaaaagtac | 1620 |
| tgtgttattg aagtaggga catgctcctg agaacttcaa taggccaggt gtcaaggccc | 1680 |
| atgttcctat acgtgagaac caatggaacc tcaaaaatta aaatgaaatg gggaatggag | 1740 |
| atgaggcgtt gcctccttca atctcttcaa caaattgaga gcatgattga ggcagagtct | 1800 |
| tctatcaaag agaaagacat gaccaaagaa ttttttgaaa acaagtcgga gatgtggccg | 1860 |
| attggagagt cacctaaggg agtggaggaa ggctccatcg ggaaggtgtg caggacatta | 1920 |
| ctagcaaaat ctgtattcaa cagcttgtat gcatctccac agctcgaggg gttttcagct | 1980 |
| gaatcaagaa aattgttact tattgttcag gcacttaggg acaacctgga acctggaacc | 2040 |
| ttcgacattg aaggactata tgaagcaatt gaggagtgcc tgattaatga tccctgggtt | 2100 |
| ttgcttaatg catcttggtt caactccttc ctcacacatg cactgaaata g | 2151 |

<210> SEQ ID NO 4
<211> LENGTH: 1695
<212> TYPE: DNA
<213> ORGANISM: Artificial Sequence
<220> FEATURE:
<223> OTHER INFORMATION: Synthesized HA gene nucleotide sequence

<400> SEQUENCE: 4

| | |
|---|---|
| atggagaaaa tagtgcttct tcttgcaata gtcagtcttg tcaaaagtga tcatatttgc | 60 |
| attggttacc atgcaaacaa ctcgacagag caggttgaca caataatgga aaagaacatt | 120 |
| actgttacac atgcccaaga catactggaa aagacacaca tgggaagct ctgcgatcta | 180 |
| aatggagtga aacctctcat tttaagagat tgtagtgtag ctgggtggct cctcggaaac | 240 |
| ccaatgtgtg acgaattcat caatgtgccg aatggtcttt acatagtgga aaggccaat | 300 |
| ccagccaatg acctctgtta cccagggat ttcaacgact atgaagaact gaaacaccta | 360 |
| ttgagcagaa taaaccattt tgagaaaata cagatcatcc ccaaaagttc ttggtccgat | 420 |

```
catgaagcct cattaggggt gagctcagca tgtccatacc agggaagttc ctcctttttc      480
agaaatgtgg tatggcttat caaaaagaac aatacatacc caacaataaa gagaagctac      540
aataatacca accaagaaga tctcttggta ctgtgggggga ttcaccatcc taatgatgag     600
gcagagcaga caaggctcta tcaaaatcca accacctata tttccgttgg acatcaaca      660 ctaaaccaga gattggtacc aaaaatagct actagatcca agtaaacgg caaagtgga       720 aggatggatt tcttttggac aattttaaaa ccgaatgatg caattaactt cgagagtaat     780
ggaaatttca ttgctccaga atatgcatac aaaattatca gaaaggggga ctcagcaatt     840
atgaaaagtg aattggaata tggtaactgc aacaccaagt gtcaaactcc aatgggggcg    900
ataaactcta gtatgccgtt ccacaacata caccccctca ccatcgggga atgccccaaa    960
tatgtgaaat caaacagatt agtccttgcg actggactca gaaataccccc tcaaagagag  1020 agcagaggac tatttggagc catagcaggt tttatagagg aggatggca gggaatggta     1080 gatggttggt atgggtacca ccatagcaat gagcagggga gtggatacgc tgcagacaaa    1140
gaatccactc aaaaggcaat agatggagtc accaataagg tcaactcgat cattgacaaa    1200
atgaacactc aatttgaggc cgttggaaag gaatttaata acttggaaag gaggatagag    1260
aatttacata gcagatgga agacggattc ctagatgtct ggacttataa tgctgaactt     1320
ctggttctca tggaaaatga gagaactcta gactttcatg actcaaatgt caagaacctt   1380
tatgacaagg tccgactaca gcttagggat aatgcaaagg agctgggtaa tggttgttc   1440 gagttctatc acaaatgtga taatgaatgt atggaaagtg taaaaaacgg aacgtatgac    1500
tacccgcagt attcagaaga agcaagacta aacagagagg aaataagtgg agtaaaattg    1560
gaatcaatgg gaacttacca aatactatca atttattcaa cagtggcgag ttccctagca    1620
ctggcaatca tggtagctgg tctatcttta tggatgtgct ccaatggatc gttacaatgc    1680
agaatttgca tttaa                                                     1695

<210> SEQ ID NO 5
<211> LENGTH: 1497
<212> TYPE: DNA
<213> ORGANISM: Artificial Sequence
<220> FEATURE:
<223> OTHER INFORMATION: Synthesized NP gene nucleotide sequence

<400> SEQUENCE: 5
atggcgcttc aaggcaccaa acgatcttat gagcagatgg aaactggtgg agaacgccag     60
aatgctactg agatcagagc atctgttggg agaatggttg gtggaatcgg aagattctac    120
atacagatgt gcactgaact caaactcagc gaccacgaag gcaggctgat ccaaaacagc    180
ataacaatag agagaatggt cctctctgca tttgatgaga ggaggaacag gtacctggaa    240
gaaaatccca gtgcggggaa ggatccgaag aaaactggag gtccaatcta caaaagaagg   300
gaaggaaagt gggtgagaga gctgattctg tatgacaaag aggagatcag agaatctgg    360 cgtcaagcga acaatggaga agacgcaact gctggtctca cccatctgat gatctggcat    420
tccaatctga atgatgccac atatcaaaga acaagagctc ttgtgcgcac tgggatggac   480
cccagaatgt gttctctgat gcaaggatca actctcccga agatcagg agctgctggt    540 gcagcagtaa agggaattgg gacaatggtg atggaactaa ttcggatgat aaagcgagga    600
atcaatgacc ggaatttctg gagaggcgac aatggacgaa gacaaggat tgcatatgag    660 agaatgtgca acatcctcaa agggaaattc caaacagcag cacaacgagc aatgatggac    720
```

| | |
|---|---|
| caagtgcggg aaagcagaaa tcctgggaat gctgaaattg aagaccttat ctttctggca | 780 |
| cggtctgcac tcattctgag aggatcagtg gcccataagt cctgtttgcc tgcttgtgtc | 840 |
| tatgggcttg ctgtagccag tggatatgac tttgagagag aagggtactc tctggtcgga | 900 |
| atagatcctt ttcgtctgct ccaaaacagc caggtgttca gcctcattag atcaaatgag | 960 |
| aacccagcac ataaaagtca actggtatgg atggcatgtc attctgcagc atttgaagac | 1020 |
| ctgagagtgt caagcttcat cagaggaaca agagtaatcc aaggggaca actgtccacc | 1080 |
| agaggtgttc aaatagcttc aaatgagaac atggaaacaa tagactccag cactcttgaa | 1140 |
| ctaagaagca gatactgggc tataaggacc aggagtggag gaaacaccaa ccaacataga | 1200 |
| gcatctgcag ggcaaatcag tgtacaacct actttctcgg tacagagaag ccttcctttc | 1260 |
| gagagagcaa ccatcatggc ggcattcaca gggaacactg aaggcagaac atccgacatg | 1320 |
| aggactgaaa tcataagaat gatggaaaat gccaaaccag aagacgtgtc tttccaaggg | 1380 |
| cggggagtct tcgagctctc ggacgaaaag gcaacgagcc cgatcgtgcc ttcctttgac | 1440 |
| atgagtaatg aaggatctta tttcttcgga gacaatgcag aggagtatga caattaa | 1497 |

<210> SEQ ID NO 6
<211> LENGTH: 1401
<212> TYPE: DNA
<213> ORGANISM: Artificial Sequence
<220> FEATURE:
<223> OTHER INFORMATION: Synthesized NA gene nucleotide sequence

<400> SEQUENCE: 6

| | |
|---|---|
| atgaatccaa atcagaagat aatagcaatt ggctctgttt ctctaactat tgcgacaata | 60 |
| tgtttcctca tgcagattgc catcttagca acgactatga cactacattt caagcagaat | 120 |
| gaatgcagca ccccctcgaa taatcaagta gtgccatgtg aaccaatcat aatagaaagg | 180 |
| aacatagtgc atttgaatag tactaccata gagaaggaaa tttgtcctaa agtgacagaa | 240 |
| tacaagaatt ggtcaaaacc acaatgtcaa attacagggt tcgctccttt ctccaaggac | 300 |
| aactcaatta ggcttccgc aggtggggat atctgggtga agagaaacc ttatgtgtcg | 360 |
| tgcggtcttg gtaaatgtta tcaatttgca cttgggcagg gaaccacttt gaaaaacaaa | 420 |
| cactcaaatg gcactacacg tgatagaatt cctcatagaa cccttttaat gaatgagttg | 480 |
| ggtgtcccgt tcatttggg aaccaaacaa gtgtgcatag catggtccag ctcaagctgc | 540 |
| catgatggga agcatggtt acatgtttgt gtcactgggg atgataaaaa tgcgactgct | 600 |
| agtatcattt atgatgggat gcttgttgac agtattggtt catggtctaa aaacatcctc | 660 |
| agaactcagg agtcagaatg cgtttgcatc aatggaactt gtacagtagt aatgactgat | 720 |
| ggaagtgcat caggaaaggc tgacactaga atactattca taagagaggg gaaaattgtt | 780 |
| cacattagcc cattgtcagg aagtgctcag catgtggagg aatgctcctg ttaccccgg | 840 |
| tatccagaag ttaggtgtgt ttgcagagac aattggaagg ctccaatag gcccgttcta | 900 |
| tatataaata tggcagatta tagtattaag tccagttatg tgtgctcagg acttgttggc | 960 |
| gacacaccaa gaaatgatga taactccagc agcagcaact gcagggatcc taataacgag | 1020 |
| agagggccc aggagtgaa agggtgggcc tttgacaatg gaaatgatat ttggatggga | 1080 |
| cgaacaatca agaggatttt acgctcaggt tatgagactt tcagggtcgt tggtggttgg | 1140 |
| accacggcta attccaagtc acagataaat agacaagtca tagttgacag tgacaactgg | 1200 |
| tctgggtatt ctggtatctt ctctgttgaa ggcaaaaact gcatcaacag tgttttttat | 1260 |
| gtggagttga taagaggaag accacaggag actaaggtgt ggtggacttc aaatagcatc | 1320 |

| | |
|---|---|
| attgtatttt gtggaacctc aggtacctat ggaacaggct catggcctga tggggcgaat | 1380 |
| atcaacttca tgcctatata a | 1401 |

<210> SEQ ID NO 7
<211> LENGTH: 982
<212> TYPE: DNA
<213> ORGANISM: Artificial Sequence
<220> FEATURE:
<223> OTHER INFORMATION: Synthesized M gene nucleotide sequence

<400> SEQUENCE: 7

| | |
|---|---|
| atgagtcttc taaccgaggt cgaaacgtac gttctctcta tcatcccgtc aggcccctc | 60 |
| aaagccgaga tcgcgcagag acttgaagat gtctttgcag ggaagaacac agatcttgag | 120 |
| gctctcatgg aatggctaaa gacaagacca atcctgtcac ctctgactaa ggggatttta | 180 |
| gggtttgtgt tcacgctcac cgtgcccagt gagcgaggac tgcagcgtag acgatttgtc | 240 |
| caaaatgccc taaatgggaa tggagaccca acaacatgg acaggcagt caaactatac | 300 |
| aagaagctga gagggagat gacattccat ggagcaaagg aagttgcact cagttattca | 360 |
| actggtgcgc ttgccagttg catgggtctc atatacaacc ggatgggaac ggtaacaaca | 420 |
| gaagtggctc ttggcctggt atgtgccact tgtgagcaga ttgctgattc acaccatagg | 480 |
| tctcacagac agatggtgac taccaccaac ccactaatca ggcatgagaa cagaatggta | 540 |
| ctagccagca ctacagctaa ggccatggag caaatggctg gctcgagcga gcaggcagcg | 600 |
| gaagccatgg aggttgcaag tcaggctagg cagatggtgc aggcgatgag gacaattggg | 660 |
| actcaaccta gctccagtgc aggtctgaaa atgatctta ttgaaaattt gcaggcctac | 720 |
| cagaaacgga tgggagtgca gatgcagcga ttcaagtgat tctctcgttg ttgcagcaag | 780 |
| tgtcattggg atattgcact tgatattgtg gattcttgat cgtcttttct tcaaatgcat | 840 |
| ttatcgtcgc tttaaatacg gtttgaaaag agggccttct acggaaggag tgcctgagtc | 900 |
| tatgagggaa gagtatcggc aggagcagca gagtgctgtg aatgttgacg atggtcattt | 960 |
| tgtcaacata gagctggagt aa | 982 |

<210> SEQ ID NO 8
<211> LENGTH: 838
<212> TYPE: DNA
<213> ORGANISM: Artificial Sequence
<220> FEATURE:
<223> OTHER INFORMATION: Synthesized NS gene nucleotide sequence

<400> SEQUENCE: 8

| | |
|---|---|
| atggattcca acactgtgtc aagcttccag gtagactgct ttctttggca tgtccgcaaa | 60 |
| cgatttgcag accaaggacg gggtgatgcc ccatttctag accggcttcg ccagatcag | 120 |
| aagtccctaa gaagaagagg cagcactctt ggtctggaca tcagaaccgc tactcatgaa | 180 |
| ggaaagcata tagtggagca gattctggag gaagagtcag atgaggcatt taaaatgact | 240 |
| attgcttcag tgctagctcc acgctaccta actgacatga ctattgaaga atgtcaagg | 300 |
| gattggttga tgctcattcc caaacagaaa gtgacagggt ctctttgcat tagaatggac | 360 |
| caagcaatag tggataaaac catcacactg aaagcaaact tcagtgttac tttcaatcga | 420 |
| ctggaagctc taatactact tagagcttt acagatgaag gggcaatagt gggcgaaatc | 480 |
| tcaccattac cttctcttcc aggacatact gatgaggatg tcaaaaatgc aattgagatc | 540 |
| ctcatcggag gatttgaatg gaatgataac acagttcgag tctctgaaac tctacagaga | 600 |

-continued ttcgcttgga gaagcagcga tgaggatggg agatctccac tctctccaaa gtagaaacgg 660
gaaatggaga gaacaattga gccagaagtt tgaagaaata agatggctga ttgaagaagt 720
gcgacatagg ttaaagatta cagagaatag ctttgaacaa ataacattta tgcaagcctt 780
gcaactattg cttgaagtgg agcaagagat aagaactttc tcgtttcagc ttatttaa 838

<210> SEQ ID NO 9
<211> LENGTH: 1842
<212> TYPE: DNA
<213> ORGANISM: Artificial Sequence
<220> FEATURE:
<223> OTHER INFORMATION: Modified rHA gene nucleotide sequence

<400> SEQUENCE: 9
atgaacactc aaatcctgat attcgctctg attacgacca ttccaacaga tgcagacaaa 60
atctgcctcg gacatcactc cgtgtcaaac ggaaccaaag taaacacatt aactgaaaaa 120
ggagtggaag tcgtcaatgc aaccgaaaca gtggaacgaa caaacacccc caggatctgc 180
tcaaaaggga aaaggacagt tgacctcggt caatgtggac tcctggggac aatcactgga 240
ccacctcaat gtgaccaatt cctaaaattt tcagccgatt taattgttga gaggcgagaa 300
ggaagtgatg tctgttatcc tggaaaattc gtgaatgaag aagctctgag gcaaattctc 360
agagaatcag gcggaattga caaggaaccc atgggattca aatacaatgg aataaggact 420
aatgggacaa ccagtgcatg taggagatca ggatcttcat tctatgcaga aatgaaatgg 480
ctcctgtcaa acacagataa tgctacattc ccgcagatga ccaagtcata taaaaataca 540
agagaaagcc cagctatagt agtatggggg atccatcatt ccgtttcaac tgcagagcaa 600
accaagctat atgggagtgg aaacaaactg gtgacagttg ggagttctaa ttatcaacaa 660
tctttcgtac cgagtccagg agcaagacca caagttaatg gtcaatctgg aagaattgac 720
tttcattggc taatactaaa tcccaatgat acagtcactt tcagtttcaa tggggctttc 780
atagctccag atcgtgcaag cttcctgaga gggaaatcta tgggaatcca gagtggagta 840
caggttgatg ccaattgtga aggggactgc tatcatagtg gagggacaat aataagtaac 900
ttgccatttc agaacataga tagcagggca gttggaaaat gtccgagata tgttaggcaa 960
aggagtcttc tgctggcaac agggatgaag aatgttcctg aggttccaaa gggaagaggc 1020
ctatttggtg ctatagcggg gttcattgaa aatggatggg aaggcctaat tgatggttgg 1080
tatggtttca gacatcaaaa tgcacaggga gagggaactg ctgcagatta caaaagcact 1140
caatcggcaa tagatcaaat aacagggaaa ttaaaccgac ttatagcaaa aaccaaccaa 1200
caatttgagt tgatagacaa tgaattcaat gaggtagaga agcaaatcgg taatgtgata 1260
aattggacca gagattctat aacagaagta tggtcataca atgctgaatt cttggtggca 1320
atggagaacc aacatacaat tgatctggct gattcagaaa tgaacaaact gtatgaacga 1380
gtgaaaagac agttgagaga gaatgctgaa gaagacggca cgggttgctt tgaaatattt 1440
cacaagtgtg atgatgactg tatggccagt attagaaata acacctatga tcacagaaaa 1500
tacagagaag aggcaatgca aaatagaata cagattgacc caatcaaact aagcagcggc 1560
tacaaagatg tgatactttg gtttagcttc ggggcatcat gtttcatact tctagccatt 1620
gtaatgggcc ttgtcttcat atgtgtgaag aatggaaaca tgcggtgcac tatttgtata 1680
ggcagcggat atattcctga ggcccctaga gatggacagg cctatgtgag aaaggatggc 1740
gaatgggtgc tgctgtctac atttctggga tccggcctga acgacatctt cgaggcccag 1800
aagatcgagt ggcacgaggg ccaccaccac caccaccact ga 1842

<210> SEQ ID NO 10
<211> LENGTH: 1455
<212> TYPE: DNA
<213> ORGANISM: Artificial Sequence
<220> FEATURE:
<223> OTHER INFORMATION: Synthesized rNA gene nucleotide sequence

<400> SEQUENCE: 10

| | | | | | |
|---|---|---|---|---|---|
| atggctcgag | tttttcagca | agatattggt | ctcagggagc | ataaagcagg | ggtcaagatg | 60 |
| aatccaaacc | agaagattct | atgcacttca | gccactgcta | tcgcaatagg | cgcaatcaca | 120 |
| gtactcattg | gaatagcaaa | cataggactg | aacataggac | tgcatctaaa | atcgggctgc | 180 |
| aattgctcac | gctcacaacc | tgaaacaacc | aacacaagcc | aaacaacaat | aaacaactat | 240 |
| tataatgaaa | caaacatcac | caacatccaa | atgggagaaa | gaacaagcag | gaatttcaat | 300 |
| aacttaacta | aagggctctg | tactataaat | tcatggcaca | tatatgggaa | agacaacgca | 360 |
| gtaagaattg | gagaaagctc | ggatgtttta | gtcacaagag | aaccctatgt | ttcatgcggc | 420 |
| ccagatgaat | gcaagttcta | tgctctcagc | caaggaacaa | caatcagagg | gaaacactca | 480 |
| aacggaacaa | tacacgatag | gtcccagtat | cgtgccctga | taagctggcc | actatcatca | 540 |
| ccgcccacag | tgtacaacag | cagggtggag | tgcatcgggt | ggtcaagtac | tagttgccat | 600 |
| gatggcaaat | ccagaatgtc | aatatgtata | tcaggaccaa | acaacaatgc | atctgcagta | 660 |
| gtatggtaca | acagacggcc | tgttgcagaa | attaacacat | gggcccgaaa | catactaaga | 720 |
| acacaggaat | ctgaatgtgt | atgccacaac | ggcgtatgcc | cagtagtgtt | caccgatggg | 780 |
| cctgccactg | gacctgcaga | cacaagaata | tactatttta | aagaggggaa | aatattgaag | 840 |
| tgggagtctc | tgattggagc | tgctaagcat | gttgaagaat | gctcatgtta | cgggaaacga | 900 |
| acagggatta | cctgcacatg | cagggacaat | tggcagggct | caaatagacc | agtgattcag | 960 |
| atagacccag | tagcaatgac | acacactagt | caatatatat | gcagtcctgt | ccttacagac | 1020 |
| agtccccgac | cgaatgaccc | aaacataggt | aagtgtaatg | acccttatcc | aggtaatgat | 1080 |
| aacaatggag | tcaagggatt | ctcatacctg | gatgggaata | cacttggct | agggaggaca | 1140 |
| ataagcacat | cctcgaggtc | tgggtacgag | atgttaaaag | tgccaaatgc | attgacagat | 1200 |
| gatagatcaa | agcccatcca | aggtcagaca | attgtattaa | acgctgactg | gagtggttac | 1260 |
| agtgggtctt | tcatagacta | ttgggctgaa | ggggactgct | atcgagcgtg | ttttatgtg | 1320 |
| gagctaatac | gtgggaaacc | caaggagggt | aaagtgtggt | ggaccagcaa | tagtatagta | 1380 |
| tcgatgtgtt | ccagtacaga | attcctggga | caatggaact | ggcctgacgg | ggctaaaata | 1440 |
| gagtacttcc | tctaa | | | | | 1455 |

<210> SEQ ID NO 11
<211> LENGTH: 17
<212> TYPE: DNA
<213> ORGANISM: Artificial Sequence
<220> FEATURE:
<223> OTHER INFORMATION: Primer pCI-EarI-1

<400> SEQUENCE: 11
tagcgagagg ccgcacg                                              17

<210> SEQ ID NO 12
<211> LENGTH: 27
<212> TYPE: DNA
<213> ORGANISM: Artificial Sequence
<220> FEATURE:

```
<223> OTHER INFORMATION: Primer pCI-EarI-2

<400> SEQUENCE: 12
tcttcgttcg gtcacagctt ctgtaag                                       27

<210> SEQ ID NO 13
<211> LENGTH: 35
<212> TYPE: DNA
<213> ORGANISM: Artificial Sequence
<220> FEATURE:
<223> OTHER INFORMATION: Terminator sequence

<400> SEQUENCE: 13
ccagggtact ggtcctgacc acgttggagg gggga                              35

<210> SEQ ID NO 14
<211> LENGTH: 39
<212> TYPE: DNA
<213> ORGANISM: Artificial Sequence
<220> FEATURE:
<223> OTHER INFORMATION: Primer LN155-HA1-F

<400> SEQUENCE: 14
tgaggttcca aagggaagag gcctatttgg tgctatagc                          39

<210> SEQ ID NO 15
<211> LENGTH: 40
<212> TYPE: DNA
<213> ORGANISM: Artificial Sequence
<220> FEATURE:
<223> OTHER INFORMATION: Primer LN155-HA1-R

<400> SEQUENCE: 15
aaataggcct cttccctttg gaacctcagg aacattcttc                         40

<210> SEQ ID NO 16
<211> LENGTH: 28
<212> TYPE: DNA
<213> ORGANISM: Artificial Sequence
<220> FEATURE:
<223> OTHER INFORMATION: Primer Bm-HA-1F

<400> SEQUENCE: 16
tattcgtctc agggagcaaa agcagggg                                      28

<210> SEQ ID NO 17
<211> LENGTH: 35
<212> TYPE: DNA
<213> ORGANISM: Artificial Sequence
<220> FEATURE:
<223> OTHER INFORMATION: Primer Bm-NS-890R

<400> SEQUENCE: 17
atatcgtctc gtattagtag aaacaagggt gtttt                              35

<210> SEQ ID NO 18
<211> LENGTH: 29
<212> TYPE: DNA
<213> ORGANISM: Artificial Sequence
<220> FEATURE:
<223> OTHER INFORMATION: Primer Bm-NA-1F

<400> SEQUENCE: 18
tattcgtctc agggagcaaa agcaggagt                                     29
```

```
<210> SEQ ID NO 19
<211> LENGTH: 36
<212> TYPE: DNA
<213> ORGANISM: Artificial Sequence
<220> FEATURE:
<223> OTHER INFORMATION: Primer Bm-NA-1413R

<400> SEQUENCE: 19
atatcgtctc gtattagtag aaacaaggag tttttt                                36

<210> SEQ ID NO 20
<211> LENGTH: 14
<212> TYPE: PRT
<213> ORGANISM: Artificial Sequence
<220> FEATURE:
<223> OTHER INFORMATION: LN155-wHA cleavage site amino acid sequence

<400> SEQUENCE: 20

Pro Glu Val Pro Lys Arg Lys Arg Thr Ala Arg Gly Leu Phe
1               5                   10

<210> SEQ ID NO 21
<211> LENGTH: 42
<212> TYPE: DNA
<213> ORGANISM: Artificial Sequence
<220> FEATURE:
<223> OTHER INFORMATION: LN155-wHA cleavage site nucleotide sequence

<400> SEQUENCE: 21
cctgaggttc caaagagaaa acggactgcg agaggcctat tt                          42

<210> SEQ ID NO 22
<211> LENGTH: 10
<212> TYPE: PRT
<213> ORGANISM: Artificial Sequence
<220> FEATURE:
<223> OTHER INFORMATION: LN155-rHA cleavage site amino acid sequence

<400> SEQUENCE: 22

Pro Glu Val Pro Lys Gly Arg Gly Leu Phe
1               5                   10
```